(12) United States Patent
Mürner et al.

(10) Patent No.: US 9,107,678 B2
(45) Date of Patent: Aug. 18, 2015

(54) LOCKING SCREW WITH SYNCHRONIZED THREAD

(75) Inventors: Beat Mürner, Reichenbach (CH); Tobias Bluechel, Selzach (CH)

(73) Assignee: Stryker Trauma SA (CH)

( * ) Notice: Subject to any disclaimer, the term of this patent is extended or adjusted under 35 U.S.C. 154(b) by 1347 days.

(21) Appl. No.: 12/455,027

(22) Filed: May 27, 2009

(65) Prior Publication Data
US 2010/0057138 A1 Mar. 4, 2010

(30) Foreign Application Priority Data

Sep. 2, 2008 (EP) .................................... 08015472

(51) Int. Cl.
 A61B 17/58 (2006.01)
 A61B 17/17 (2006.01)
 A61B 17/80 (2006.01)

(52) U.S. Cl.
 CPC .......... A61B 17/1735 (2013.01); A61B 17/1728 (2013.01); A61B 17/8057 (2013.01); A61B 17/80 (2013.01); A61B 17/8047 (2013.01)

(58) Field of Classification Search
 CPC . A61B 17/80; A61B 17/8057; A61B 17/1728
 USPC ................................................. 606/291, 308
 See application file for complete search history.

(56) References Cited

U.S. PATENT DOCUMENTS

| | | | | |
|---|---|---|---|---|
| 5,360,452 A | * | 11/1994 | Engelhardt et al. | 623/22.37 |
| 5,851,207 A | | 12/1998 | Cesarone | |
| 5,954,722 A | * | 9/1999 | Bono | 606/281 |
| 6,730,091 B1 | * | 5/2004 | Pfefferle et al. | 606/70 |
| 7,063,701 B2 | | 6/2006 | Michelson | |
| 7,179,260 B2 | | 2/2007 | Gerlach et al. | |
| 7,635,365 B2 | * | 12/2009 | Ellis et al. | 606/71 |
| 7,766,916 B2 | | 8/2010 | Leyden et al. | |
| 7,799,062 B2 | | 9/2010 | Crozet | |
| 7,951,176 B2 | | 5/2011 | Grady, Jr. et al. | |

(Continued)

FOREIGN PATENT DOCUMENTS

| | | |
|---|---|---|
| EP | 1 661 525 | 5/2006 |
| EP | 1 661 526 | 5/2006 |

(Continued)

OTHER PUBLICATIONS

European Search Report, EP 11177140 dated Oct. 18, 2011.

*Primary Examiner* — Bruce E Snow
*Assistant Examiner* — Melissa Hoban
(74) *Attorney, Agent, or Firm* — Lerner, David, Littenberg, Krumholz & Mentlik, LLP (57) ABSTRACT

A bone fixation system includes a bone plate and a bone screw having a threaded head. The inner surface of the bone plate is adapted for facing a bone surface on which the plate is mounted. The outer surface of the bone plate faces away from the bone surface. A through opening extends from the inner surface to the outer surface of the plate wherein the through opening comprises a guiding portion and a blocking portion. The guiding portion of the opening is provided with a guiding thread for guiding a thread of a shaft of the bone screw. The blocking portion is provided with a blocking thread for blocking a thread of the head of the bone screw. The blocking thread has a larger diameter than the guiding thread and the guiding portion is located closer to the inner bone plate surface than the blocking portion.

5 Claims, 6 Drawing Sheets

(56) References Cited

U.S. PATENT DOCUMENTS

| | | |
|---|---|---|
| 2003/0153919 A1 | 8/2003 | Harris |
| 2004/0059334 A1* | 3/2004 | Weaver et al. .................. 606/69 |
| 2005/0038444 A1 | 2/2005 | Binder et al. |
| 2005/0043738 A1 | 2/2005 | Ryan |
| 2005/0165400 A1* | 7/2005 | Fernandez ...................... 606/69 |
| 2005/0192578 A1* | 9/2005 | Horst .............................. 606/69 |
| 2005/0228398 A1 | 10/2005 | Rathbun et al. |
| 2005/0234467 A1 | 10/2005 | Rains |
| 2005/0261688 A1 | 11/2005 | Grady, Jr. et al. |
| 2006/0095044 A1 | 5/2006 | Grady, Jr. et al. |
| 2006/0100637 A1 | 5/2006 | Rathbun et al. |
| 2006/0116680 A1 | 6/2006 | Kugler et al. |
| 2006/0264946 A1 | 11/2006 | Young |
| 2007/0142921 A1* | 6/2007 | Lewis et al. ................ 623/22.36 |
| 2008/0188899 A1 | 8/2008 | Bottlang et al. |
| 2011/0224737 A1 | 9/2011 | Lewis et al. |
| 2012/0109216 A1 | 5/2012 | Austin et al. |

FOREIGN PATENT DOCUMENTS

| | | |
|---|---|---|
| EP | 1878394 A2 | 1/2008 |
| GB | 2437492 A | 10/2007 |
| JP | 2006-150054 A | 6/2006 |
| JP | 2007-500069 A | 1/2007 |
| JP | 2007-507296 A | 3/2007 |

* cited by examiner

LOCKING SCREW WITH SYNCHRONIZED THREAD

BACKGROUND OF THE INVENTION

The present invention relates to a locking screw with a synchronized thread as well as a bone plate having a corresponding synchronized thread. Further, the present invention relates to a targeting device for applying a bore tool or a screw to a bone plate, and in particular to a targeting device which corresponds to the bone plate with respect to a coupling.

For treatments of bone fractures by surgery, in particular cases it is necessary to use bone plates and corresponding bone screws for a fixation of fragments of a bone. One of the rising problems when applying a bone plate and a bone screw to a bone is that the bone screw may untighten or become loose with respect to the bone plate, which may result in a bad healing process of the bone fracture, and further may lead to complications during the healing process. Therefore, it is necessary to lock the bone screw with respect to the bone or with respect to the bone plate to avoid the untightening or loosing of the bone screw, while maintaining a sufficient guiding of the screw during application of the screw.

In the past, several solutions for this problem have been proposed, for example to apply an additional fixation plate onto the head of the bone screw in order to press the head of the bone screw against the bone plate. Further, some locking mechanisms have been used in order to block or to clamp the head of the bone screw in the through hole of the bone plate. However, most of the commonly known solutions lack of a particular guiding of the bone screw with respect to the bone plate.

SUMMARY OF THE INVENTION

It is one aspect of the present invention to provide a bone screw and a bone plate as well as a targeting device which allow a guided insertion of a bone screw into a bone plate and a bone, and to provide a secure locking.

According to an exemplary embodiment of the invention there is provided a bone plate comprising an inner surface being adapted for facing a bone surface to which the bone plate is to be mounted, an outer surface being adapted for facing away from a bone surface to which the bone plate is to be mounted. A through opening extends from the inner surface to the outer surface, wherein the through opening comprises a guiding portion and a blocking portion. The guiding portion is provided with a guiding thread for guiding a thread of a shaft of a bone screw, and the blocking portion is provided with a blocking thread for blocking a thread of a head of a bone screw, wherein the blocking portion is wider than the guiding portion and the guiding portion is located closer to the inner surface than the blocking portion.

Thus, it is possible to apply a corresponding bone screw and to guide a shaft of a bone screw by the guiding portion of the bone plate to ensure that the bone screw can be applied in a predetermined orientation with respect to a bone. When inserting the bone screw into the through opening, the shaft of a bone screw may be guided by the guiding portion when being screwed in, and afterwards, when the bone screw is screwed-in into a bone plate down to a sufficient deep position, a bone screw may enter the blocking portion, wherein a corresponding thread on the head of the bone screw may engage the blocking thread for blocking the thread of the head of a bone screw. Thus, the bone screw can be guided during application with respect to the predetermined application direction as well as the feed forward, which is predetermined by the dimensioning of the guiding thread.

Further, a targeting tool may be applied to the bone plate so that the targeting tool and the bone plate may be coupled. The targeting tool may be coupled to the blocking portion of the bone plate so that the guiding portion remains free for guiding purposes. A bone screw may be screwed-in into the bone plate while the targeting device is coupled to the bone plate. After having screwed-in the screw to a particular depth, the targeting tool may be removed by decoupling it from the bone plate and pulling its coupling portion over a head of the screw. Then the screw can be finally screwed in.

According to an exemplary embodiment of the invention, there is provided a bone plate, wherein a pitch of the blocking thread and a pitch of the guiding thread correspond to each other with respect to inclination and phase of corresponding threads of a bone screw to be guided and locked.

Thus, the bone screw may engage the guiding thread when entering the through opening with a corresponding thread on a shaft of a bone screw, and later a thread on a head of the bone screw can engage the blocking thread of the bone plate. Owing to the corresponding inclination and phase of the corresponding guiding thread and blocking thread, no unintended blocking will occur when screwing in the bone screw into the bone plate. Moreover, the bone screw can be designed to not extend over the outer surface of the bone plate in its final position in order to avoid any injury. When screwing in the bone screw into the through opening, the bone screw can be locked, when the head of the bone screw reaches a transit edge between the blocking portion and the guiding portion.

According to one exemplary embodiment of the invention, the bone plate is provided with a gap portion, which is axially provided between the guiding portion and the blocking portion, and the blocking portion radially protrudes towards a centre axis over the gap portion. Thus, the gap portion allows a space to be provided for entering a bottom head of a bone screw and to receive any remaining particles which are displaced or disposed during screwing-in the bone screw into the through opening of the bone plate.

According to one exemplary embodiment of the invention, the blocking thread comprises a double lead thread.

Thus, it is possible to provide a constant gap between adjacent grooves of the blocking thread and the guiding thread, even if the diameter of the blocking portion is larger than the diameter of the guiding portion, maintaining a corresponding inclination of the blocking thread and the guiding thread.

According to one embodiment of the invention, the through opening comprises a tapered portion, wherein the tapered portion is wider than the blocking portion, wherein the tapered portion is located closer to the outer surface than the blocking portion.

Thus, it is also possible to apply a commonly used bone screw instead of a particularly adapted bone screw. In other words, it is possible to apply a bone screw without a thread at the head of the bone screw. Commonly used bone screws often have a rounded bottom edge, so that such a commonly used bone screw can be applied to the inventive bone plate.

According to one exemplary embodiment of the invention, the tapered portion comprises a spherically shaped tapering.

Thus, it is possible to fix a bone screw with a variable angle of the longitudinal axis of the bone screw with respect to the bone plate, i.e. the screw and the plate may have a variable angle to each other. In other words, such a bone plate may be used together with a bone screw having corresponding threads on the head and the shaft corresponding to the blocking portion and the guiding portion of the bone plate, as well as bone screws which allow a variable angle.

According to another embodiment of the invention, there is provided a bone screw having a screw shaft and a screw head, wherein the screw shaft comprises a self-cutting thread, the self-cutting thread being adapted for self-cutting a corresponding thread in a bore of a bone, wherein the screw head is provided with a blocking thread, wherein the blocking thread is wider than the self-cutting thread.

Thus, a bone screw may be provided, which may be guided in a corresponding bone plate as described above, and when being screwed in, may be secured by a threaded screw head, which engages to a corresponding blocking portion of a bone plate.

According to an exemplary embodiment of the invention, the bone screw is provided, wherein a pitch of the blocking thread and a pitch of the self-cutting thread correspond to each other with respect to inclination and phase of corresponding threads of a bone plate to be mounted by the bone screw.

Thus, the bone screw can be applied to the bone plate described above, wherein the guiding portion of the bone plate may guide the screw by the engaged self-cutting thread of the shaft when being screwed in, wherein the threaded head of the bone screw may engage into the blocking portion without any unintended early blocking. Thus, the head of the bone screw can totally sink below the outer surface of the bone plate in order to avoid unintended injuries.

According to another aspect of the invention the bone screw comprises a distal portion, wherein the distal portion is axially provided between the self-cutting thread and the screw head, and the self-cutting thread radially protrudes to the outside over the distal portion. Thus, a particular distal portion allows a free space to receive for example remaining tissue during application of the bone screw into the bone plate, so that any unintentionally blocking can be avoided before reaching a predetermined position of the bone screw with respect to the bone plate.

According to one aspect of the invention the bone screw is cannulated. Thus, for example a Kirschner-wire or k-wire can be applied or a further improved positioning of the bone screw.

According to an aspect of the invention, there is provided a combination of an inventive bone plate and an inventive bone screw.

According to an additional aspect of the invention, there is provided a targeting device for applying a bore tool or a screw to a bone plate, wherein the targeting device comprises an outer sleeve having a through bore in an axial direction and a coupling portion, wherein the coupling portion is connected in axial direction to a first end of the outer sleeve, wherein the coupling portion comprises an exterior thread portion and a through hole having a corresponding exit to the through bore of the outer sleeve, wherein the exterior thread portion being adapted to be screwed in into a corresponding blocking thread of a bone plate, wherein the outer sleeve comprises two slits extending in axial direction to the first end of the outer sleeve forming two arms, wherein the coupling portion comprises two slits in axial direction dividing the coupling portion in two parts, wherein the slits of the outer sleeve continue into the respective slits of the coupling portion, so that the parts of the coupling portion are movable in a direction perpendicular to the axial direction.

Thus, the targeting device can be used for applying a bore tool or a screw into a bone plate by screwing-in the targeting device with the exterior thread portion of the coupling portion into a corresponding thread—for example the blocking thread—of a bone plate. After applying an inventive bone screw through the through bore of the outer sleeve and the corresponding through bore of the coupling portion, the bone screw can be screwed in into the guiding thread of the bone plate to a certain depth. After having screwed in the bone screw into the guiding thread of the bone plate, the targeting device can be screwed-out out of the blocking thread of the bone plate, so that the blocking thread of the bone plate is released from the targeting device for receiving the corresponding head of the bone screw. In order to remove the targeting device from the bone screw, the two arms of the targeting device can be moved outwards to release a space, so that the coupling portion can be moved over the head of the bone screw. It should be noted that a direction perpendicular to the longitudinal axis also includes a direction having a directional component of a direction perpendicular to the longitudinal axis. In other words, any movement away from the longitudinal axis may provide a releasing of the head of the screw. Afterwards, the bone screw can be further screwed in into the through opening of the bone plate and the head of the bone screw can be blocked into the blocking thread of the bone plate. Thus, the targeting device does not only serve for a pre-guiding procedure before and when inserting the bone screw into the bone plate, but may also serve as a protection sleeve for protecting the surrounding tissue during surgery.

According to an exemplary embodiment of the invention, the targeting device comprises an inner sleeve having an outer contour and a through bore in axial direction, wherein the outer sleeve of the targeting device having an inner contour, wherein the inner sleeve is releasably connectable within the through bore of the outer sleeve, wherein at least a part of the outer contour of the inner sleeve fits the inner contour of the outer sleeve for keeping the slit coupling portion in shape.

Thus, it can be avoided that the both arms supporting the coupling parts and the thread portions of the coupling parts can unintendedly move inwardly, resulting in an unintentional release of the thread portion of the coupling portion from the blocking thread of the bone plate. In other words, the inner sleeve serves as a support for the arms of the outer sleeve in order to keep the slit coupling portion and the threading arrangement in shape.

According to yet another aspect of the invention, the bore of the coupling portion is of a smaller diameter than the through bore of the outer sleeve, wherein a transit between the through bore of the coupling portion and the through bore of the outer sleeve is a smooth transit.

According to an aspect of the invention, the inner sleeve is movable along an axial direction with respect to the outer sleeve, urging the arms to move outwardly when abutting to the transit.

Thus, it is possible to move the arms of the outer sleeve by urging the inner sleeve to the transit portion between the coupling portion and the outer sleeve, so that no unintended forces may be applied to the head of a bone screw when removing the targeting device from the bone plate. In other words, instead of pulling the targeting device over the head of the bone screw and moving the arms outwardly by pulling it over the head of the bone screw, the inner sleeve may be moved against the transit portion, urging the arms to move outwardly, so that no additional forces may act on the head of the bone screw, in particular, when the bone screw is not fully screwed-in into the bone plate and the bone. The inner diameter of the inner sleeve may be larger than the axial bore of the coupling portion in order to allow the insertion of a screw head.

According to an aspect of the invention, the inner sleeve and the outer sleeve each comprise corresponding defining means being adapted for defining an axial position with respect to each other. Thus, an unintended movement of the inner sleeve and the outer sleeve may be avoided, for example when applying the targeting device to the bone plate. Such a defining means may be for example a threading portion, wherein outer threading on the inner sleeve may engage to an inner thread of the outer sleeve.

According to one aspect of the invention, there may be provided a combination of an inventive bone plate and an inventive targeting device, wherein the thread of the coupling device engages into the blocking thread of the bone plate.

It should be noted that the above features may also be combined. The combination of the above features may also lead to synergetic effects, even if not explicitly described in detail.

These and other aspects of the present invention will become apparent from and elucidated with reference to the embodiments described hereinafter.

BRIEF DESCRIPTION OF THE DRAWINGS

Exemplary embodiments of the present invention will be described in the following with reference to the following drawings.

DETAILED DESCRIPTION

Figure 1:
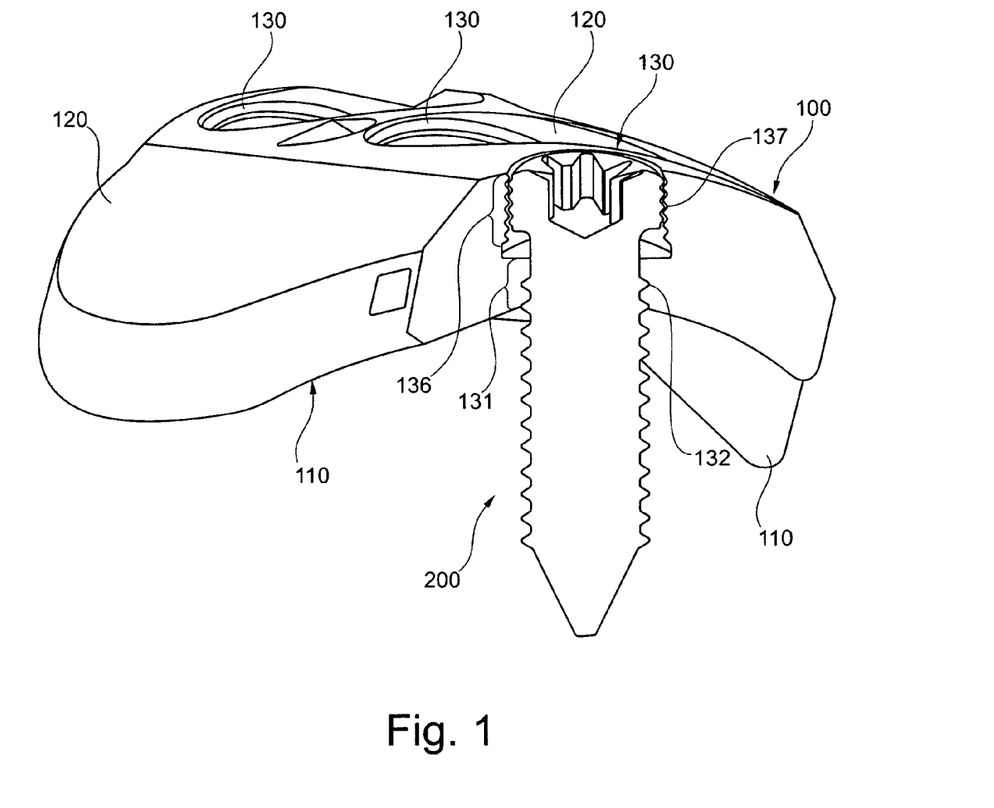
FIG. 1 illustrates an exemplary embodiment of a bone plate and a bone screw according to the invention.

FIG. 1 illustrates a bone plate and a bone screw according to a preferred embodiment of the invention. The bone plate 100 is provided with an inner surface 110 facing a bone, and an outer surface 120 facing away from a bone surface. Further, the bone plate 100 is provided with a through opening 130. The through opening 130 comprises a blocking portion 136 and a guiding portion 131. The blocking portion comprises a blocking thread 137, wherein the guiding portion 131 comprises a guiding thread 132. The guiding thread 132 and the blocking thread 137 correspond to each other with respect to inclination and phase, so that the bone screw 200 can be screwed-in through the through opening 130 of the bone plate 100. Owing to the corresponding threads 132, 137, the bone screw 200 can be screwed in without having an unintentional blocking owing to not synchronized threading portions. Thus, a blocking of the head of the bone screw 200 can take place for example when having screwed in the bone screw 200 down to a predetermined target position. The embodiment described in FIG. 1 is for example used as a locking screw in a mono-axial locking hole.

Figure 2A:
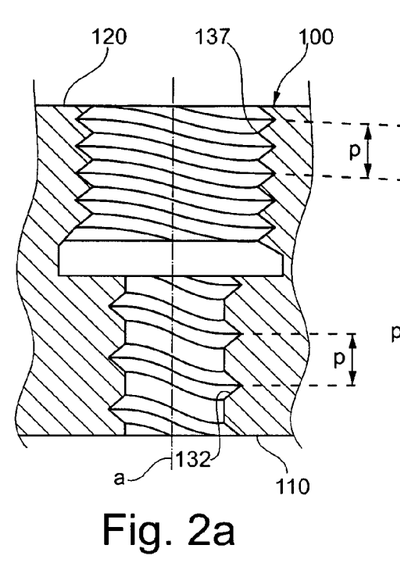
FIGS. 2A and 2B illustrate a cross-sectional view of two different embodiments of the bone plate according to the invention.
Figure 2B:
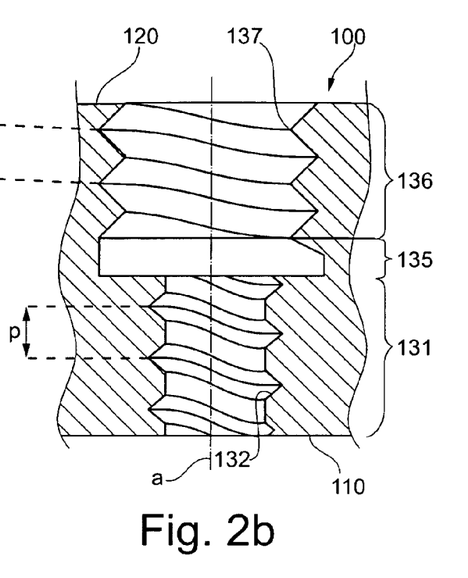

FIG. 2A illustrates a cross-sectional view of an inventive bone plate, wherein the through opening comprises a blocking thread 137 and a guiding thread 132. The pitch of the guiding thread 132 corresponds to the pitch of the blocking thread 137. Owing to the different diameters of the blocking portion and the guiding portion, the blocking thread 137 may be a double thread allowing a finer threading portion. It should be noted that also a triple thread or more can be used. As an alternative, FIG. 2B illustrates an embodiment of a bone plate 100, which has a similar guiding portion 131 like the embodiment of the FIG. 2A. However, the embodiment of FIG. 2B has a blocking thread 137 which is a single lead thread, which may be useful for example when having a small geometry, so that the threading grooves can be made wider and deeper, to be of less sensitive for damages. It should be noted that the pitch of the guiding thread 132 and the pitch of the blocking thread 137 is the same, which leads to a uniform feed forward when screwing-in a corresponding bone screw. In both FIGS. 2A and 2B, the through opening is provided with a gap portion 135, which allows a defined blocking on the transition edge from the blocking portion to the guiding portion.

Figure 3A:
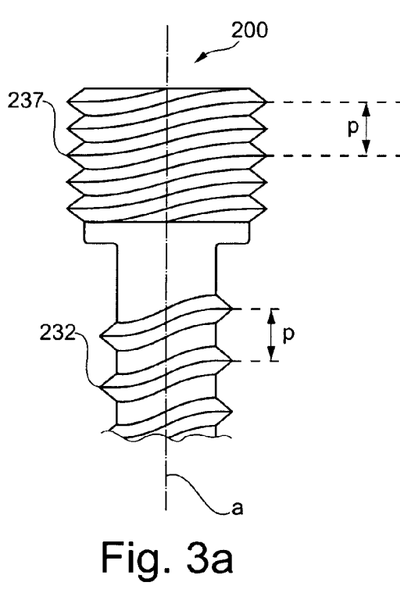
FIGS. 3A and 3B illustrate two different embodiments of a bone screw according to the invention corresponding to FIGS. 2A and 2B, respectively.
Figure 3B:
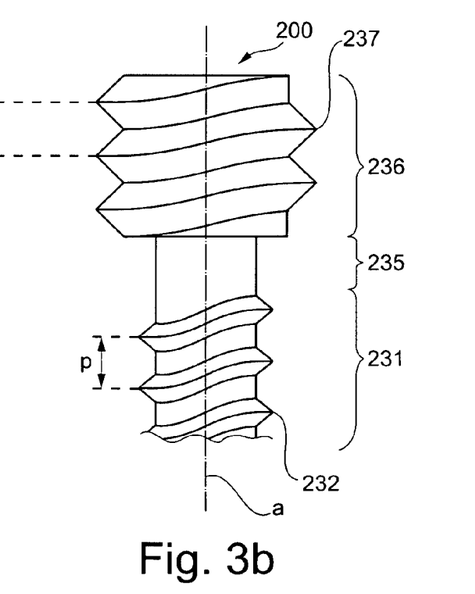

FIG. 3A illustrates a side view of a bone screw, corresponding to a bone plate illustrated in FIG. 2A. The screw head of the screw 200 has a lead thread 237 with a pitch corresponding to the pitch of a guiding thread 232. FIG. 2B illustrates an alternative embodiment of a bone screw corresponding to the bone plate of FIG. 2B. The blocking portion 236 comprises a blocking thread 237 of a single lead thread. The guiding portion 231 comprises a guiding thread 232, which is similar to that of FIG. 3A. It should be noted that the pitch of the blocking thread 237 and the guiding thread 232 is the same, allowing an unhindered feed forward into a corresponding through opening of a bone plate. Although the pitch of the blocking thread and the guiding thread is the same, the distance between the blocking thread and the guiding thread does not have to be mandatorily a multiple of the pitch, since the entry of the respective threads may be of a different phase. However, it should be noted that it is important that the blocking thread and the guiding thread correspond with respect to inclination on the one hand and on a matching combination of a distance to each other and a phase, in order to meet the corresponding threads of the bone plates. The bone screws of FIG. 3A and FIG. 3B further comprise a gap portion 235 allowing a defined blocking of the bone screw within the through opening of the bone plate 100, in particular in the corresponding gap portion thereof.

Figure 4:
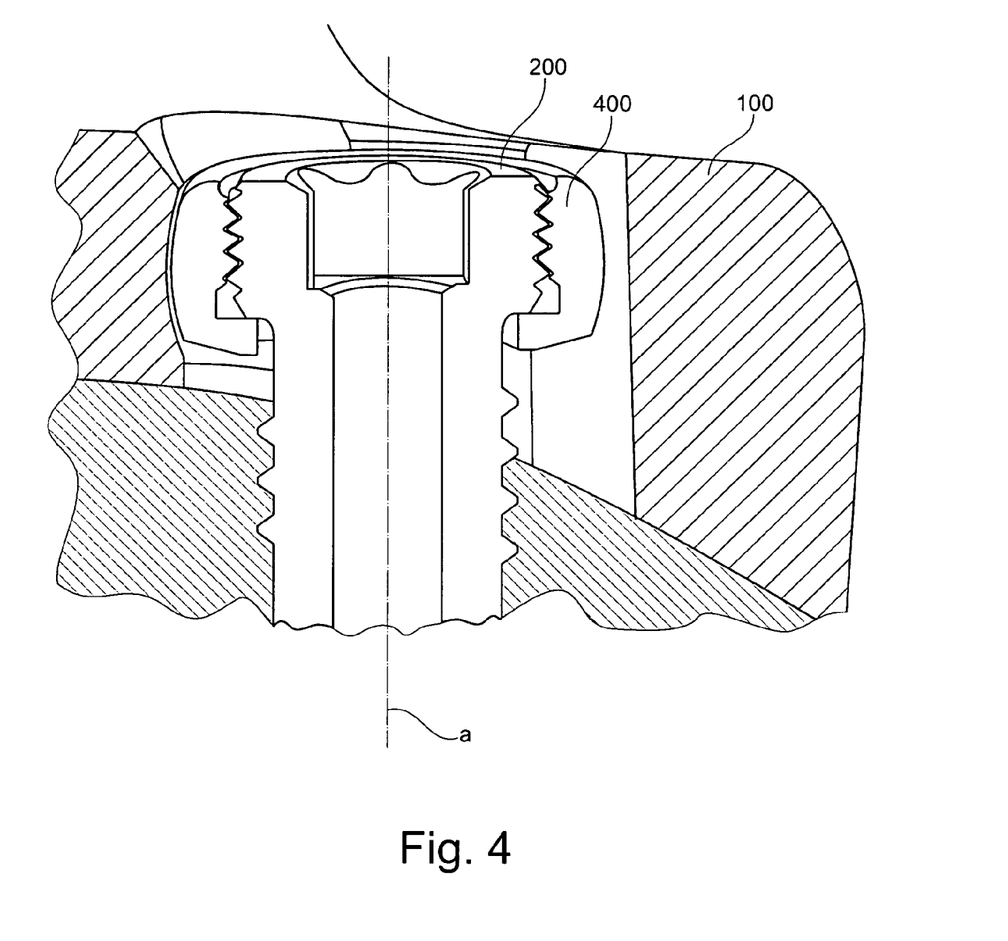
FIG. 4 illustrates a bone screw and a bone plate according to an exemplary embodiment of the invention.

FIG. 4 illustrates a further embodiment of the present invention, where the bone plate 100 is provided with an additional locking ring 400. The locking ring 400 is fixed in a particular hole of the bone plate, wherein the locking ring provides the blocking thread and the blocking portion. The bone screw 200 can be screwed-in into the corresponding thread of the locking ring 400, in order to be blocked with respect to the fixed locking ring and therefore to the bone plate 100. With this arrangement, it is possible to predetermine an axis with respect to the bone plate 100, since the polyaxial locking ring may be inserted with different axial angles in order to provide different accesses for inserting the bone screw 200 into a bone plate. It should be noted that the polyaxial locking ring may also be provided with a guiding portion and a guiding thread, although not explicitly illustrated.

Figure 5:
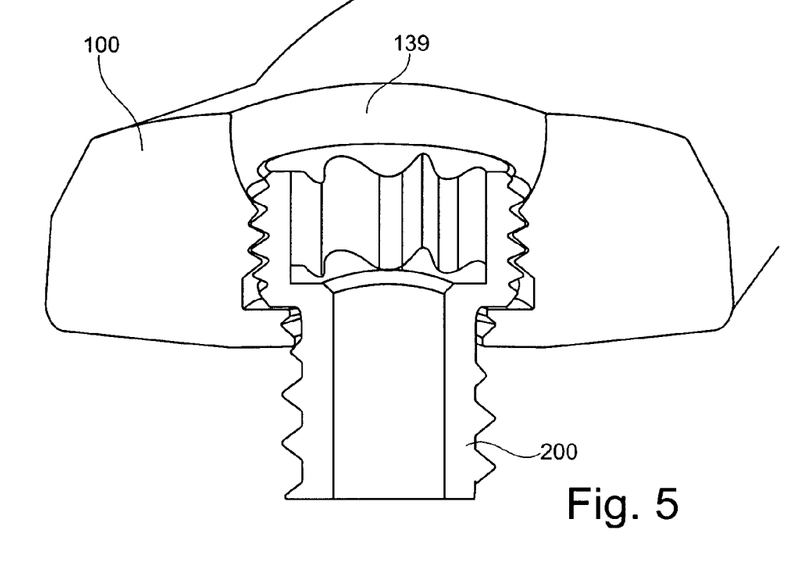
FIG. 5 illustrates a further exemplary embodiment of the invention.
Figure 6:
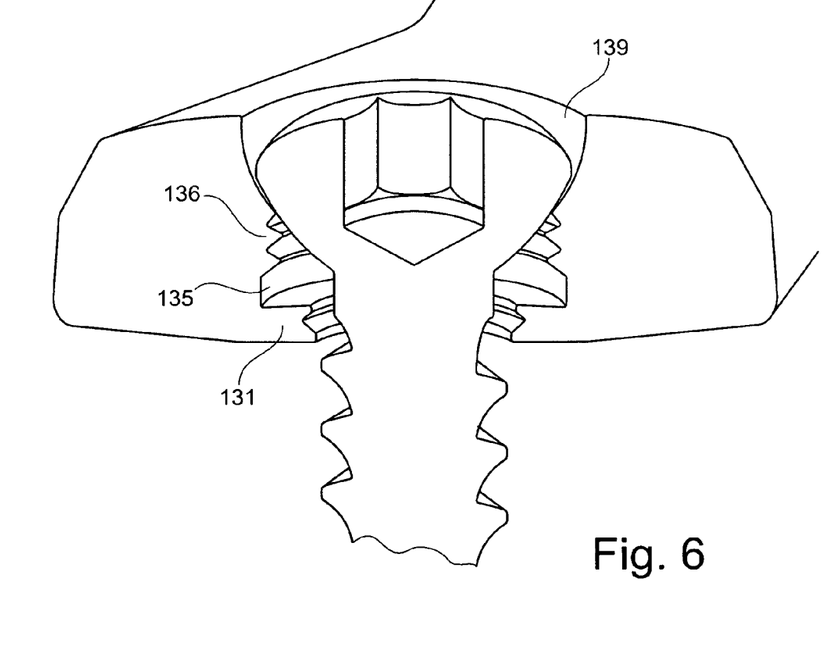
FIG. 6 illustrates a further exemplary embodiment of a bone plate according to the invention.

The bone screw 200 can be cannulated with a cannulation 401, as can be seen from FIG. 4, in order to apply for example a Kirschner-wire, also known as K-wire (not shown). The cannulation further allows one to obtain a securing of the screw in order to avoid unintentional loss of the screw in the surrounding tissue during surgery FIG. 5 illustrates a bone plate according to an exemplary embodiment of the invention, wherein the through opening comprises a tapered portion 139. The tapered portion 139 starts at the outer surface of the bone plate and ends downwardly to the inlet of the blocking thread. Thus, the bone plate of the embodiment shown in FIG. 5 can be used together with a bone screw according to the invention 200. FIG. 6 illustrates the same bone plate 100, however, a commonly known bone screw is inserted into the through opening of the bone plate. In the embodiment shown in FIG. 6, the commonly known bone screw resides on the tapered portion 139 instead of the threaded portion 137. The commonly used bone screw does not mandatorily have to use the guiding portion 131. Thus, FIG. 5 and FIG. 6 illustrate the different use of one and the same bone plate 100 with different bone screws.

Figure 7:
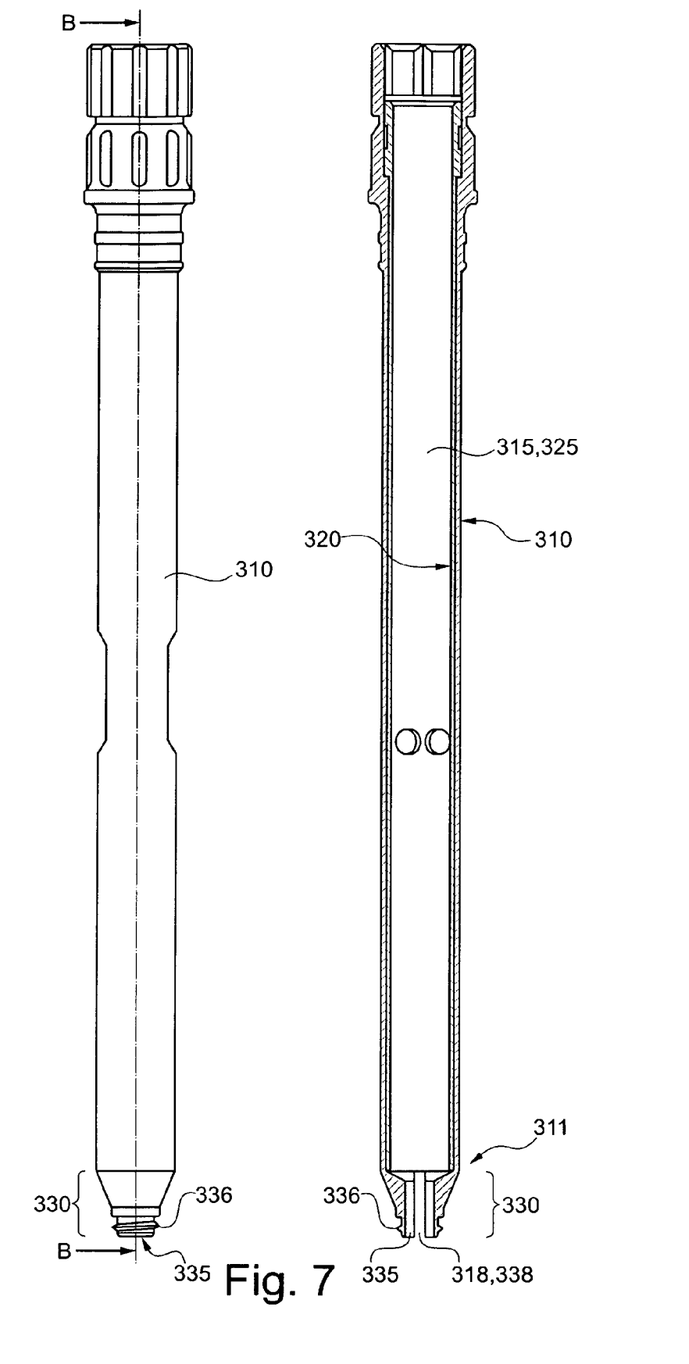
FIG. 7 illustrates an outer view and a cross-sectional view of a targeting device according to an exemplary embodiment of the invention.

FIG. 7 illustrates a targeting device according to an exemplary embodiment of the invention. The targeting device comprises an outer sleeve 310 and a coupling portion 330. The coupling portion comprises a threading portion 336, which is adapted to be coupled to a blocking thread of a corresponding bone plate. The coupling portion 330 is fixedly connected to a first end 311 of the outer sleeve 310. The outer sleeve has a through bore 325, which corresponds with respect to the longitudinal axis to a through bore 335 of the coupling portion 330. Further, the outer sleeve as well as the coupling portion is provided with a pair of slits 318, 338, wherein the slits 338 of the coupling portion 330 correspond to respective slits 318 of the outer sleeve 310, such that the slits 318 succeed into the slits 338. Thus, the slits form resilient arms of the targeting device, which allow to release a certain space at the coupling portion 330, to allow to move the targeting device, i.e. the coupling portion thereof, around a screw thread. In other words, when applying the targeting device to a bone plate, the targeting device will be screwed-in into the blocking thread 137 of the blocking portion 136. After fixing the targeting device to the bone plate, a screw may be inserted through the through bore 315 to be inserted into the through opening of the bone plate. When being screwed in into the guiding portion of the bone plate, the targeting device may be removed by screwing out and to move the arms outwardly, so that the narrower parts of the coupling portion 330 can be moved outwardly to be moved around the head of the bone screw.

The targeting device of FIG. 7 further comprises an inner sleeve 320 having a through bore 325. The inner sleeve 320 may serve for keeping the outer shape of the coupling portion and the threading portion, and to avoid any inwardly moving of the arms, leading to an unintended releasing of the threaded portion 336 from a corresponding blocking portion of the bone plate. The inner sleeve 320 having a through bore 325 that may be fixed by for example a spring ring arrangement keeping the inner sleeve 320 in a predetermined position. The inner sleeve may be moved in axial direction with respect to the outer sleeve. The distal end of the inner sleeve may abut to a transit portion between the outer sleeve and the coupling portion. The transit portion may be for example a tapered portion. The abutting distal end may move the resilient arms outwardly to release a space. Thus, the narrow bore 335 will be widened to release a screw head.

Figure 8:
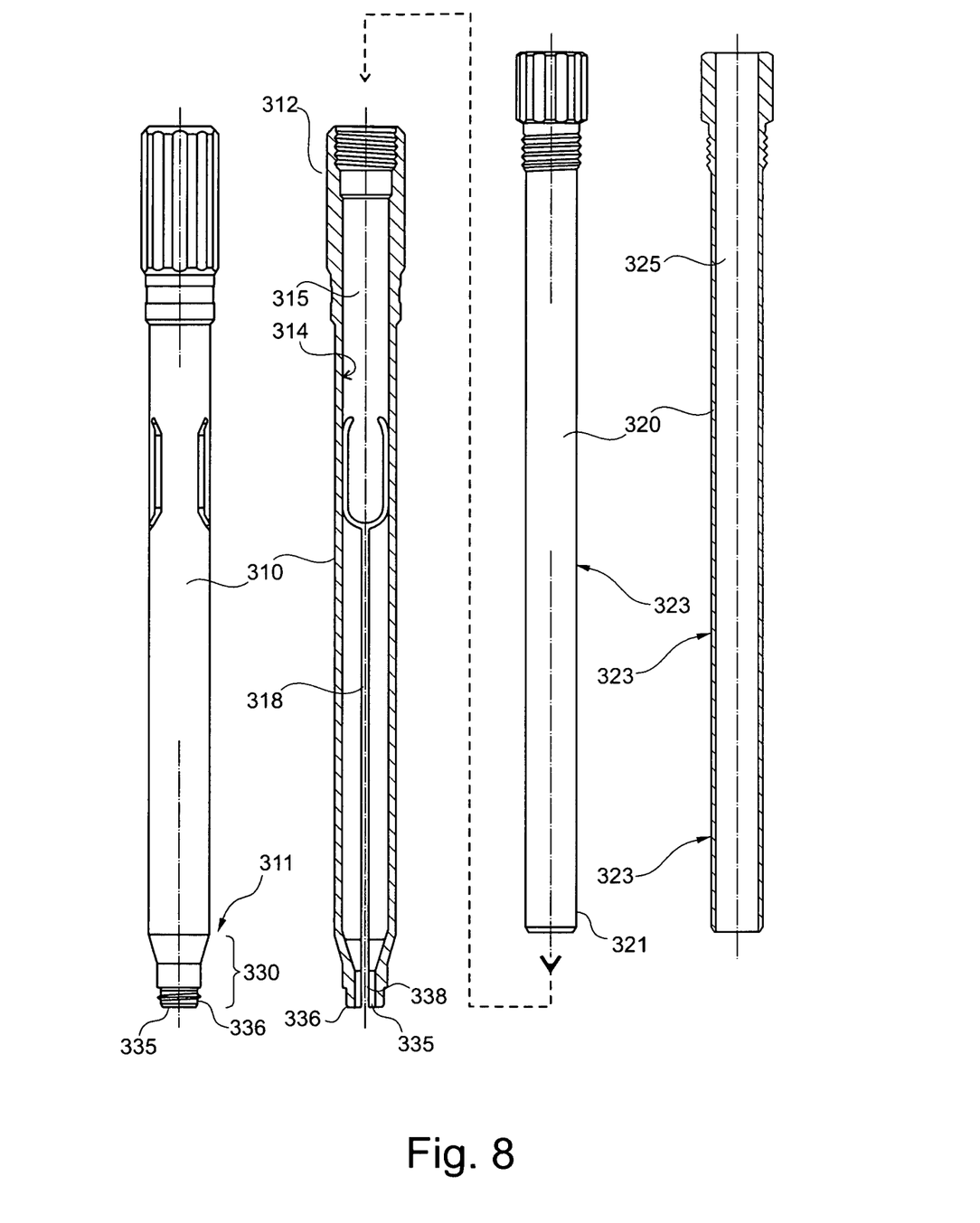
FIG. 8 illustrates an outer view and a cross-sectional view of an outer sleeve and an inner sleeve of a targeting device according to an exemplary embodiment of the invention.

FIG. 8 illustrates an alternative embodiment of a targeting device. The outer sleeve 310 is provided with a slit 318, which slit divides into two parallel slits 319 in a direction towards a second end 312 of the outer sleeve 310. The dividing into two parallel slits 319 increases the elasticity of the arms and provides a predetermined bending area. This decreases the necessary forces to remove the connecting portion 330 from a head of the bone screw. The inner sleeve 320 may be inserted into the outer sleeve 310. The inner sleeve 320 comprises a bore through 325 in order to provide a channel to supply a bone screw towards the first end 311 of the outer sleeve 310. The bore through may have a diameter larger than the diameter of the bore through 335 of the connection portion 330. The inner sleeve 320 may be moved in axial direction into the outer sleeve 310 so that a first end 321 of the inner sleeve 320 may urge against a transition portion 340 between the outer sleeve 310 and a coupling portion 330. This transit portion 330 may be designed as a smooth transition, so that the inner sleeve 320 by moving towards the coupling portion 330 within the outer sleeve 310 can urge the arms outwardly by pushing the arms outwardly. Thus, the arms may release a certain distance for releasing a head of a bone screw without the need to have an additional force impact on the head of the bone screw. Thus, an unintended removal of the bone screw from the bone plate by the targeting device may be avoided when urging the arms outwardly by moving the inner sleeve 320 in axial direction towards the connecting portion 330.

Thus, the frequent problem that soft tissue may complicate an easy insertion of screws may be overcome. Most drill sleeves in the art need to be removed before the screw insertion, so that the screw hole position and direction is lost after the drill sleeve removal. In bad bone quality, it sometimes occurs that the screw is not sufficiently guided by the drilled hole and creates a new trajectory. The targeting device may serve as a guide for the hole insertion process for example for a polyaxial locking screw from drilling to screw insertion. The sleeve may be fixed in the thread of either a monoaxial hole or a polyaxial locking ring. The targeting device gives the screw the right trajectory and thus prevents cross-threading between screw and hole and facilitates the insertion process. The targeting device can be screwed in the desired screw hole, in particular a blocking thread of either a monoaxial plate hole or a polyaxial locking ring, and fastened for example by hand. In polyaxial locking rings, the screw direction may be adjusted as desired. The screw sleeve may have the same thread as the locking screw head. Now, a drill process and pre-tapping can be carried out with appropriate sleeves or a K-wire can be set. Now, also a targeting device may be removed and a screw can be inserted into the cannulation of a screw sleeve. The screw may be screwed in until a mark on a screwdriver showing the preliminary end position of the screw head. At this point, the threaded screw head has not reached the plate hole yet since the screw and the thread of the targeting device are equal. The outer sleeve of the targeting device can be pulled back, and the slotted sleeve tip jumps over the screw head. The screwdriver does not need to be removed. The screw head may be screwed in into the plate and may be tightened.

It should be noted that the term "comprising" does not exclude other elements and the "a" or "an" does not exclude a plurality. Also elements described in association with different embodiments may be combined.

It should be noted that reference signs in the claims shall not be construed as limiting the scope of the claims.

The invention claimed is:
1. A bone fixation system comprising
   a bone screw having a screw shaft and a head;
   wherein the screw shaft comprises a self-cutting thread having a constant first diameter, the self-cutting thread being adapted for self-cutting a corresponding thread in a bore of a bone;
   wherein the screw head is provided with a blocking thread having a constant second diameter;

wherein the constant second diameter is larger than the constant first diameter;

a bone plate having a bone facing surface and an opposite surface facing away from the bone, the bone plate having a through bore therein for receiving the bone screw, the bore having a first threaded bore portion with a constant first diameter thread adjacent the bone contacting surface for engaging the screw self-cutting thread first constant diameter and a second threaded bore portion with a constant second diameter adjacent the opposite surface for engaging the blocking thread second constant diameter, the first and second threaded bore portions being coaxial;

the first constant diameter self-cutting thread of the screw shaft engaging both the constant diameter first threaded portion of the bore of the bone plate and the bone when the constant second diameter blocking thread of the screw head is fully seated in the second threaded bore portion of the plate having the constant second diameter;

wherein a pitch (p) of the blocking thread and a pitch (p') of the self-cutting thread are the same, and wherein the blocking thread and the self-cutting thread correspond with respect to inclination and phase to corresponding threads of the bone plate to be mounted by the bone screw; and wherein the through bore of the bone plate further comprises a non-threaded circumferentially extending gap portion which is coaxially aligned with the coaxial central axis of the guiding portion and the blocking portion, wherein the non-threaded circumferentially extending gap portion has a larger diameter than the blocking portion.

2. The bone fixation system of claim 1, wherein a gap portion is axially provided between the self-cutting thread and the screw head of the bone screw, and the self-cutting thread has a larger diameter than the non-threaded circumferentially extending gap portion.

3. A bone fixation system comprising:
a bone screw having a threaded shaft with a constant first diameter and a threaded head having a constant second diameter;

a bone plate having an inner surface being adapted for facing a bone surface on which the bone plate is to be mounted; and an outer surface being adapted for facing away from a bone surface on which the bone plate is to be mounted, the bone plate having a bore therethrough extending from the inner surface to the outer surface, wherein the bore comprises a guiding bore portion and a blocking bore portion each having a central axis which are coaxially aligned;

wherein the guiding bore portion is provided with a constant diameter guiding thread for receiving and guiding the threaded shaft of the bone screw and the blocking bore portion is provided with a constant diameter blocking thread for receiving the threaded head, so that the threaded shaft of the bone screw engages both the guiding thread and a bone when the threaded head is fully seated in the blocking portion;

wherein the bone screw shaft first thread diameter is less than the head thread second diameter and the bone plate blocking thread has a larger diameter than the guiding thread and the guiding bore portion is located closer to the inner surface of the bone plate than the blocking bore portion;

wherein a pitch (p) of the blocking thread and a pitch (p') of the guiding thread are the same, and wherein the blocking thread and the guiding thread correspond with respect to inclination and phase to corresponding threads of the bone screw to be guided and blocked; and wherein the through bore of the bone plate further comprises a non-threaded circumferentially extending gap portion which is coaxially aligned with the coaxial central axis of the guiding portion and the blocking portion, wherein the non-threaded circumferentially extending gap portion has a larger diameter than the blocking portion.

4. The bone fixation system as set forth in claim 3 wherein the bone screw head threads and shaft threads have a corresponding thread pitch (P).

5. The bone fixation system as set forth in claim 3 wherein the screw head thread has double the lead of the screw shaft thread.

* * * * *